(12) United States Patent
Tahmasebi Maraghoosh et al.

(10) Patent No.: US 9,717,481 B2
(45) Date of Patent: Aug. 1, 2017

(54) METHOD OF ADJUSTING FOCAL ZONE IN ULTRASOUND-GUIDED PROCEDURES BY TRACKING AN ELECTROMAGNETIC SENSOR THAT IMPLEMENTED ON A SURGICAL DEVICE

(71) Applicant: KONINKLIJKE PHILIPS N.V., Eindhoven (NL)

(72) Inventors: Amir Mohammad Tahmasebi Maraghoosh, Ridgefield, CT (US); Vijay Parthasarathy, Mount Kisco, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/761,201

(22) PCT Filed: Jan. 15, 2014

(86) PCT No.: PCT/IB2014/058281
§ 371 (c)(1),
(2) Date: Jul. 15, 2015

(87) PCT Pub. No.: WO2014/111853
PCT Pub. Date: Jul. 24, 2014

(65) Prior Publication Data
US 2015/0342572 A1 Dec. 3, 2015

Related U.S. Application Data
(60) Provisional application No. 61/753,588, filed on Jan. 17, 2013.

(51) Int. Cl.
*A61B 8/00* (2006.01)
*A61B 5/06* (2006.01)
(Continued)

(52) U.S. Cl.
CPC ............... *A61B 8/54* (2013.01); *A61B 5/062* (2013.01); *A61B 8/0841* (2013.01); *A61B 8/461* (2013.01);
(Continued)

(58) Field of Classification Search
CPC .................... A61B 5/06; A61B 8/0841; A61B 5/065–5/066
See application file for complete search history.

(56) References Cited

U.S. PATENT DOCUMENTS 6,677,985 B1 1/2004 Kubota
2006/0193504 A1* 8/2006 Salgo .................. A61B 8/0833
382/128

(Continued)

FOREIGN PATENT DOCUMENTS

EP 2160978 A1 3/2010
WO WO2011107404 * 9/2011 ............... A61B 8/08
(Continued)

OTHER PUBLICATIONS

Peikari, Mohammad et al "Effects of Ultrasound Section-Thickness on Brachytherapy Needle Tip Localization Error", MICCAI 2011, Part 1, LNCS 6891, pp. 299-306.
(Continued)

*Primary Examiner* — Serkan Akar (57) ABSTRACT

A method and system track a location of an object while the object is disposed within a region of interest within biological tissue, the location of the object being determined with respect to a tracking coordinate frame; generate acoustic images of the region of interest, the acoustic images being generated with respect to an acoustic image coordinate frame which is different from the tracking coordinate frame; transform the location of the object from the tracking coordinate frame to the acoustic image coordinate frame;
(Continued)

and automatically adjust at least one image resolution parameter of the acoustic images in response to the location of the object with respect to the acoustic image coordinate frame.

20 Claims, 8 Drawing Sheets

(51) Int. Cl.
    *A61B 8/08*           (2006.01)
    *A61B 34/20*         (2016.01)
    *A61B 90/00*         (2016.01)

(52) U.S. Cl.
    CPC ............ *A61B 8/5238* (2013.01); *A61B 34/20* (2016.02); *A61B 2034/2051* (2016.02); *A61B 2090/364* (2016.02); *A61B 2090/378* (2016.02)

(56) References Cited

U.S. PATENT DOCUMENTS

| | | |
|---|---|---|
| 2006/0270934 A1 | 11/2006 | Savord |
| 2007/0232882 A1 | 10/2007 | Glossop |
| 2010/0081920 A1 | 4/2010 | Whitmore |
| 2010/0298705 A1* | 11/2010 | Pelissier ................. A61B 5/06 600/443 |
| 2012/0203306 A1* | 8/2012 | Sarvazyan ........... A61B 8/0841 607/61 |
| 2012/0321154 A1* | 12/2012 | Korsten ............... A61B 8/0833 382/128 |
| 2013/0041252 A1* | 2/2013 | Vignon ................ A61B 8/0841 600/424 |

FOREIGN PATENT DOCUMENTS

| | | | |
|---|---|---|---|
| WO | WO2011138698 | * 10/2011 | ............ A61B 8/08 |
| WO | 2012018851 A1 | 2/2012 | |
| WO | 2013001424 A2 | 1/2013 | |

OTHER PUBLICATIONS

Chen, Thomas Kuiran et al "A Real-Time Freehand Ultrasound Calibration System with Automatic Acuracy Feedback and Control", Ultrasound in Medicine and Biology, vol. 35, No. 1, 2009, pp. 79-93.

* cited by examiner

METHOD OF ADJUSTING FOCAL ZONE IN ULTRASOUND-GUIDED PROCEDURES BY TRACKING AN ELECTROMAGNETIC SENSOR THAT IMPLEMENTED ON A SURGICAL DEVICE

TECHNICAL FIELD

This invention pertains to an acoustic imaging system and method, and in particular to a system and method for automatic adjusting the focal zone of an acoustic imaging system during an ultrasound-guided medical procedure.

BACKGROUND AND SUMMARY

Figure 1A:
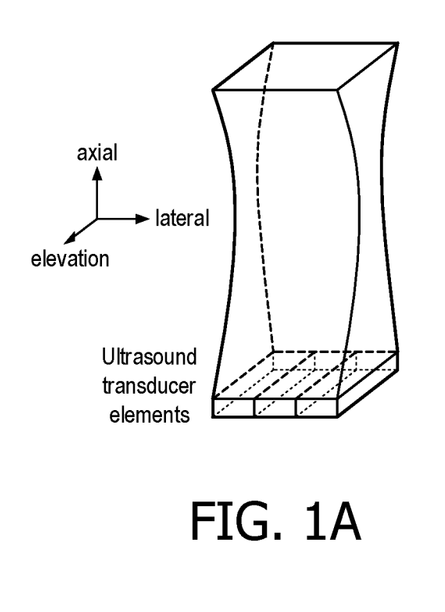
FIGS. 1A, 1B, 1C and 1D illustrate the concepts of axial, lateral, elevation, and temporal resolutions in an acoustic imaging apparatus.
Figure 1B:
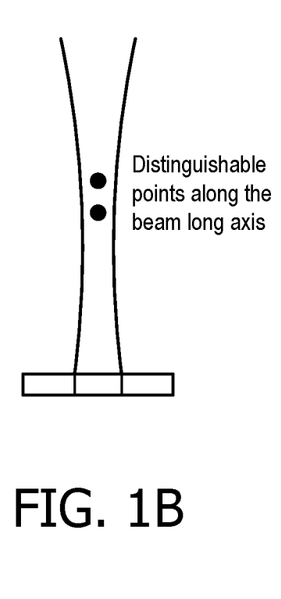
Figure 1C:
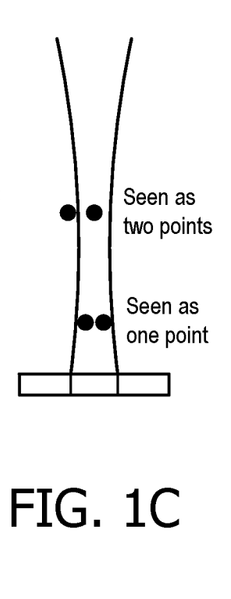
Figure 1D:
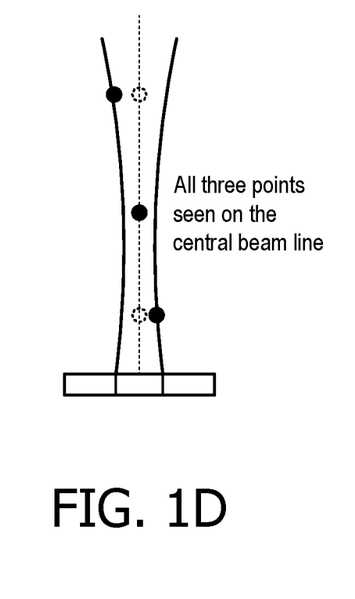

In acoustic imaging, resolution refers to the ability of an acoustic imaging apparatus to differentiate between two objects that are spatially or temporally separated from each other. It is known that acoustic image quality (or resolution) mainly depends on four factors: axial, lateral, elevation, and temporal resolutions. See, e.g., M. Peikari et al., "Effects of Ultrasound Section-Thickness on Brachytherapy Needle Tip Localization Error," 14TH INTERNATIONAL CONFERENCE ON MEDICAL IMAGE COMPUTING AND COMPUTER-ASSISTED INTERVENTION (MICCAI), 2011. FIG. 1A illustrates the relationship between axial, lateral, and elevation directions in an acoustic imaging apparatus. As illustrated in FIG. 1B, axial resolution depends on the ability of the acoustic imaging apparatus to distinguish two objects lying at different depths, parallel to the direction of the acoustic beam. Axial resolution depends on the acoustic pulse length (in general, it is roughly equal to one half of the pulse length). As illustrated in FIG. 1C, lateral resolution refers to the ability of the acoustic imaging apparatus to distinguish between two objects lying beside one another and perpendicular to the acoustic beam. The lateral resolution depends on the distance between adjacent element beams (i.e., the beam width). As illustrated in FIG. 1D, the elevation resolution is the acoustic slice thickness. Finally, the temporal resolution refers to the frame rate of the acoustic imaging apparatus.

In general, an acoustic imaging apparatus has several scales for adjusting such image resolution parameters. When the acoustic beam is emitted from the acoustic transducer(s), it has a narrow width, but the width is not a uniform width at all depths of the image. Instead, it converges at the point of the "focal zone," and becomes wider as it proceeds distally. The focal zone is the thinnest part of the acoustic beam.

Figure 2:
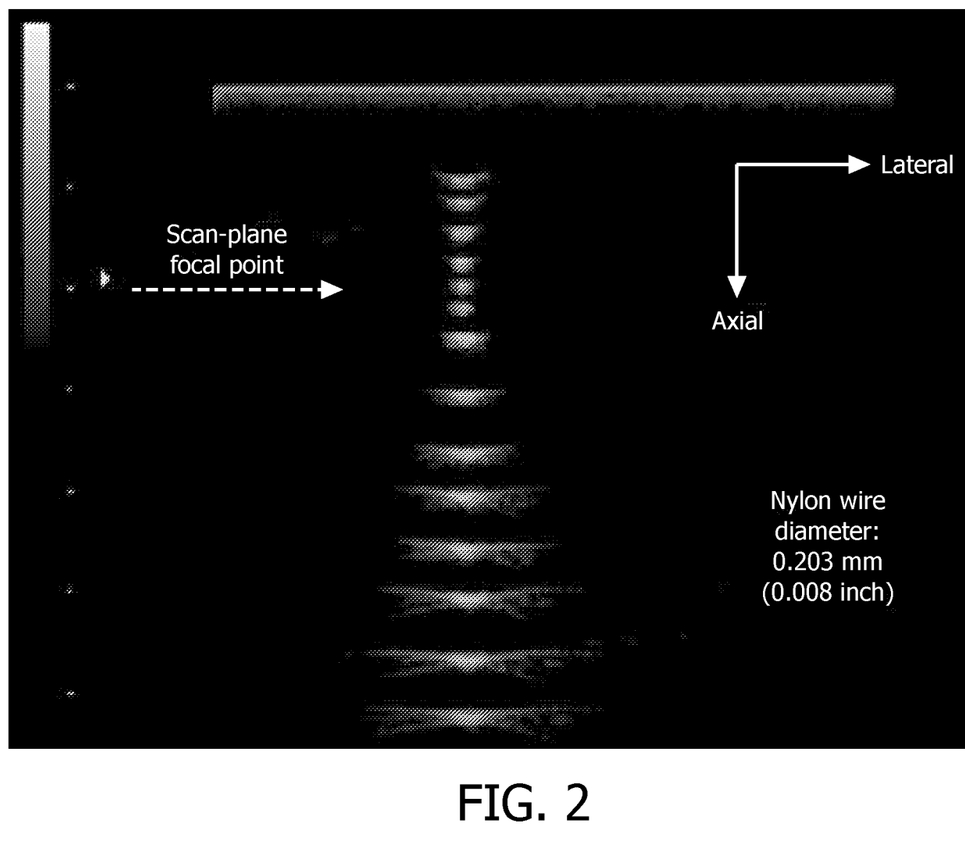
FIG. 2 illustrates the effects of axial resolution and lateral resolution on the appearance of the cross-section of a nylon wire in an acoustic image.

As can be seen for example in FIG. 2, optimization of the depth and beam focus setting makes a substantial difference in the quality of the acoustic images (see T. K. Chen et al., "A Real-Time Freehand Ultrasound Calibration System with Automatic Accuracy Feedback and Control," ULTRASOUND IN MED. & BIOL., Vol. 35, No. 1, pp. 79-93, (2009)). In particular, FIG. 2 illustrates the effects of axial resolution and lateral resolution on the appearance of the cross-section of a nylon wire in an acoustic image. The axial resolution does not change with the image depth; however, the lateral width of the dot is directly proportional to the lateral resolution.

Typically, in ultrasound-guided medical procedures such as brachytherapy the physician visually locates the current position of the needle tip (or catheter tip) on a display screen or monitor. Furthermore, a physician may visually locate the current position of the needle on a display screen or monitor when performing other medical procedures, such as biopsy procedures for the prostate and liver. The needle tip appears as bright spot in the image on the display screen. Accurate localization of the needle is a challenging problem due to existing artifacts in acoustic images. It has been shown that acoustic images may contain a number of artifacts caused by both within-plane (axial and lateral beam axes) and orthogonal-to-the-plane (elevation beam width) acoustic beam formation.

Proper adjustment of imaging parameters can help reduce artifacts and as a result, reduce error in localization of the needle tip. In particular, in order to reduce such image artifacts the focal zone (narrowest part of the acoustic beam) should be adjusted to focus the zone at the exact location of the needle tip.

Currently, such adjustments are manually controlled by the operator of the acoustic imaging apparatus. For example, during a brachytherapy procedure, the clinical physician visually identifies the approximate location of the needle tip and manually adjusts the gain, beam focus and depth of the acoustic imaging apparatus, accordingly.

However, this can be quite challenging since the non-uniform beam formation along the acoustic slice (lateral resolution) may cause errors in accurate localization of the needle tip. This can become quite tedious, time consuming, and even produce erroneous results due to human eye error.

Accordingly, it would be desirable to automatically adjust the focus of an acoustic beam employed by an acoustic imaging system, and the resulting acoustic images, to match the position of a surgical implement, e.g., the tip of a needle, during a medical procedure without the need for manual adjustment by the operator.

In one aspect of the invention, a method comprises: receiving location data from an electromagnetic tracking apparatus, the location data indicating a location of an object being tracked by the electromagnetic tracking apparatus within a region of interest within biological tissue, the data indicating the location of the object with respect to an electromagnetic tracking coordinate frame employed by the electromagnetic tracking apparatus; employing a processor to transform the location data from the electromagnetic tracking coordinate frame to an acoustic image coordinate frame employed by an acoustic imaging apparatus which is configured to employ an acoustic beam to generate acoustic image data for displaying acoustic images of the region of interest, where the acoustic image coordinate frame is different from the electromagnetic tracking coordinate frame; using the transformed data to generate at least one command for the acoustic imaging apparatus to cause the acoustic imaging apparatus to adjust at least one image resolution parameter employed by the acoustic imaging apparatus to cause the acoustic images to be focused at the location of the object; and communicating the at least one command over a communication channel to the acoustic imaging apparatus.

In some embodiments, the object is a surgical implement and the location data indicates a location of a tip of the surgical implement.

In some versions of these embodiments, the surgical implement is a needle having an electromagnetic sensor disposed at the tip.

In some embodiments, the at least one image resolution parameter includes at least one of a focal length of the acoustic beam, an image depth of the acoustic beam, a time gain compensation, and a zoom window, employed by the acoustic imaging apparatus.

In some versions of these embodiments, the image resolution parameter includes at least one of the focal length and the image depth of the acoustic beam.

In some embodiments, the communication channel comprises an Internet connection.

In some embodiments, transforming the location data from the electromagnetic tracking coordinate frame to the acoustic image coordinate frame comprises using a first transform which transforms the location data from the electromagnetic tracking coordinate frame to a reference coordinate frame and a second transform which transforms the location data from the reference coordinate frame to the acoustic image coordinate frame.

In some embodiments, the method further comprises performing a calibration procedure to produce calibration parameters, and employing the calibration parameters to transform the location data from the electromagnetic tracking coordinate frame to the acoustic image coordinate frame.

In another aspect of the invention, an apparatus comprises: an input configured to receive location data from an electromagnetic tracking apparatus, the location data indicating a location of an object being tracked by the electromagnetic tracking apparatus within a region of interest within biological tissue, the data indicating the location of the object with respect to an electromagnetic tracking coordinate frame employed by the electromagnetic tracking apparatus; a processor configured to transform the location data from the electromagnetic tracking coordinate frame to an acoustic image coordinate frame employed by an acoustic imaging apparatus which is configured to employ an acoustic beam to generate acoustic image data for displaying acoustic images of the region of interest, where the acoustic image coordinate frame is different from the electromagnetic tracking coordinate frame, and to use the transformed data to generate at least one command for the acoustic imaging apparatus to cause the acoustic imaging apparatus to adjust at least one image resolution parameter employed by the acoustic imaging apparatus to cause the acoustic images to be focused at the location of the object; and an output configured to communicate the at least one command over a communication channel to the acoustic imaging apparatus.

In some embodiments, the input and the output comprise an Internet connection.

In some embodiments, the object is a surgical implement and the location data indicates a location of a tip of the surgical implement.

In some versions of these embodiments, the surgical implement is a needle having an electromagnetic sensor disposed at the tip.

In some embodiments, the at least image resolution parameter includes at least one of a focal length of the acoustic beam, an image depth of the acoustic beam, a time gain compensation, and a zoom window, employed by the acoustic imaging apparatus.

In some versions of these embodiments, the at least one image resolution parameter includes at least one of the focal length and the image depth of the acoustic beam.

In some embodiments, transforming the location data from the electromagnetic tracking coordinate frame to the acoustic image coordinate frame comprises using a first transform which transforms the location data from the electromagnetic tracking coordinate frame to a reference coordinate frame and a second transform which transforms the location data from the reference coordinate frame to the acoustic image coordinate frame In yet another aspect of the invention, a method comprises: tracking a location of an object while the object is disposed within a region of interest within biological tissue, the location of the object being determined with respect to a tracking coordinate frame; generating acoustic images of the region of interest, the acoustic images being generated with respect to an acoustic image coordinate frame which is different from the tracking coordinate frame; employing a processor to transform the location of the object from the tracking coordinate frame to the acoustic image coordinate frame; and automatically adjusting at least one image resolution parameter of the acoustic images in response to the location of the object with respect to the acoustic image coordinate frame.

In some embodiments, an acoustic imaging apparatus generates the acoustic images of the region of interest, and wherein automatically adjusting at least one image resolution parameter of the acoustic images in response to the location of the object comprises receiving at least one command at the acoustic imaging apparatus via a communication channel to which the acoustic imaging apparatus is connected.

In some versions of these embodiments, the at least one command causes the acoustic imaging apparatus to adjust at least one of a focal length, an image depth, a time gain compensation, and a zoom window, employed by the acoustic imaging apparatus.

In some versions of these embodiments, the communication channel employs an Ethernet protocol.

In some embodiments, transforming the location of the object from the tracking coordinate frame to the acoustic image coordinate frame comprises using a first transform which transforms the location data from the tracking coordinate frame to a reference coordinate frame and a second transform which transforms the location data from the reference coordinate frame to the acoustic image coordinate frame

DETAILED DESCRIPTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention.

Figure 3:
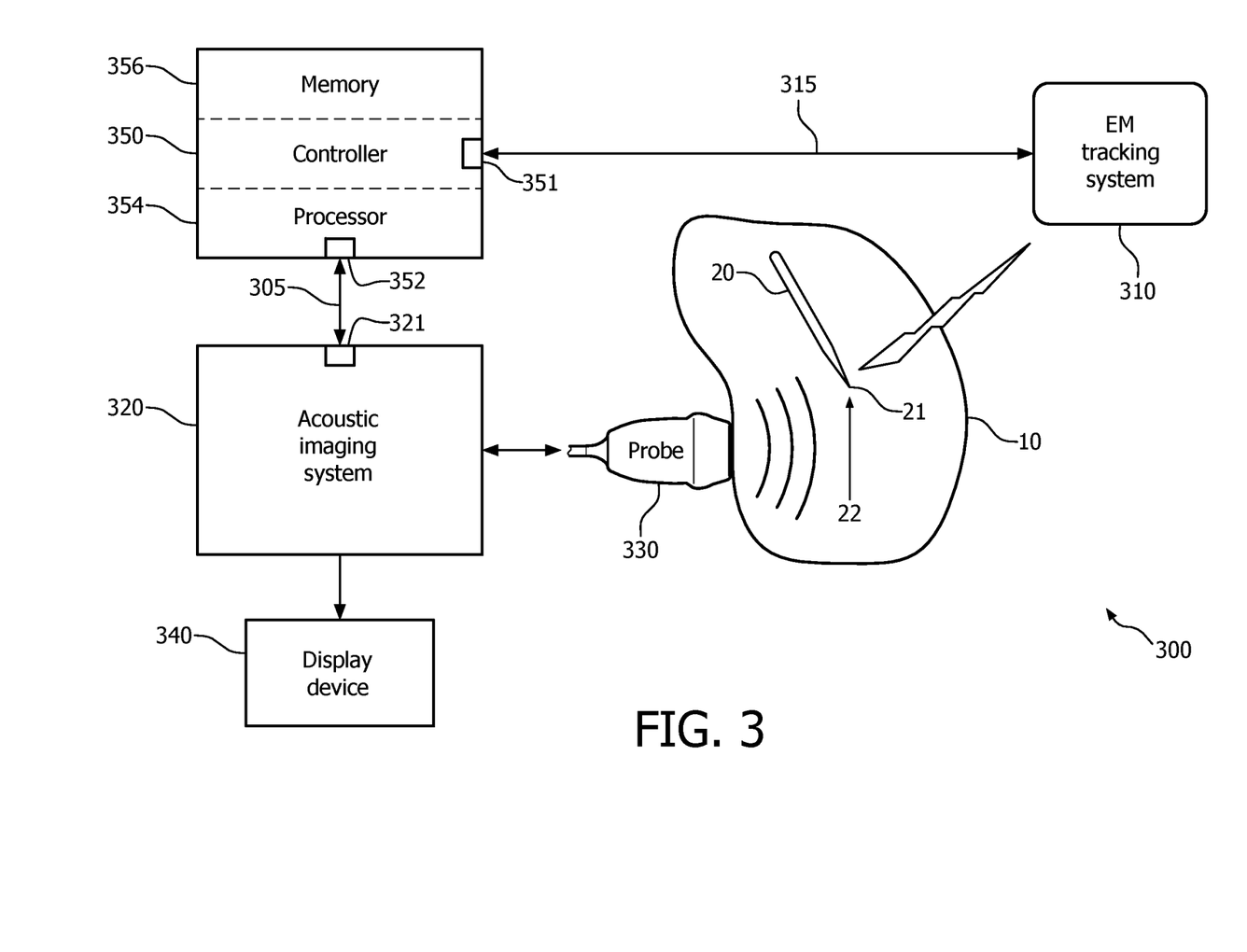
FIG. 3 is a functional block diagram of one embodiment of an arrangement for generating acoustic images which track the location of an object within a region of interest.

FIG. 3 is a functional block diagram of one embodiment of an arrangement 300 for generating acoustic (e.g., ultrasound) images which track the location of an object within a region of interest. Arrangement 300 includes an electromagnetic (EM) tracking system 310, an acoustic (e.g., ultrasound) imaging system 320, an acoustic probe 330, a display device 340, and a controller 350.

Also shown in FIG. 3 are a region of interest 10 in biological tissue (e.g., a human body), and an object 20, which in this particular example is a surgical implement, more specifically a needle. To provide a concrete illustration and example, the description to follow will refer to object 20 as needle 20, but in general it should be understood that the principles to be explained below could be applied to a variety of different objects, including a variety of different surgical implements or instruments. Needle 20 includes an EM sensor or transducer 22, for example disposed at a tip 21 of needle 20.

Controller 350 may include a processor 354 and memory 356. Memory 356 may include volatile memory such as random access memory, and/or nonvolatile memory, such as read only memory and/or FLASH memory. Among other things, memory 356 may store software or program code that is configured to cause processor 354 to execute one of more algorithms, for example various algorithms described herein, and in particular an algorithm as described below with respect to FIG. 8. Controller 350 may have one or more inputs 351 and one or more outputs 352 which may be connected to one or more communication channels, such as communication channel 305 and communication channel 315. In some embodiments, an input 351 and an output 352 of controller 350 may comprise a common input/output. In some embodiments, an input/output of controller 350 may comprise an Ethernet port for connecting to an Ethernet network. In some embodiments, communication channel 305 and communication channel 315 may include the Internet. In some embodiments, some or all of the functions of controller 350 may reside within components (e.g., a processor) of acoustic imaging system 320 or EM tracking system 310.

Acoustic probe 330 includes a plurality of acoustic transducers configured to transmit an acoustic beam into region of interest 10, and for receiving acoustic echoes or reflections from region of interest 10. Acoustic probe 330 is connected to and operates under control of acoustic imaging system 320. Acoustic imaging system 320 generates acoustic image data from the signal(s) received from acoustic probe 330, and operates with display device 340 to display the acoustic image data as acoustic images. Acoustic imaging system 320 also operates to control electrical signals which are applied to the acoustic transducers in acoustic probe 330. By controlling the relative magnitudes and phases of these electrical signals, acoustic imaging system 320 and acoustic probe 330 are able to steer the direction and focal depth of the transmitted acoustic beam to a desired focal zone, which in general also becomes the focal zone for acoustic probe 330 to receive back acoustic echoes or reflections. This may be referred to hereafter as the focal zone of acoustic imaging system 320.

Figure 4:
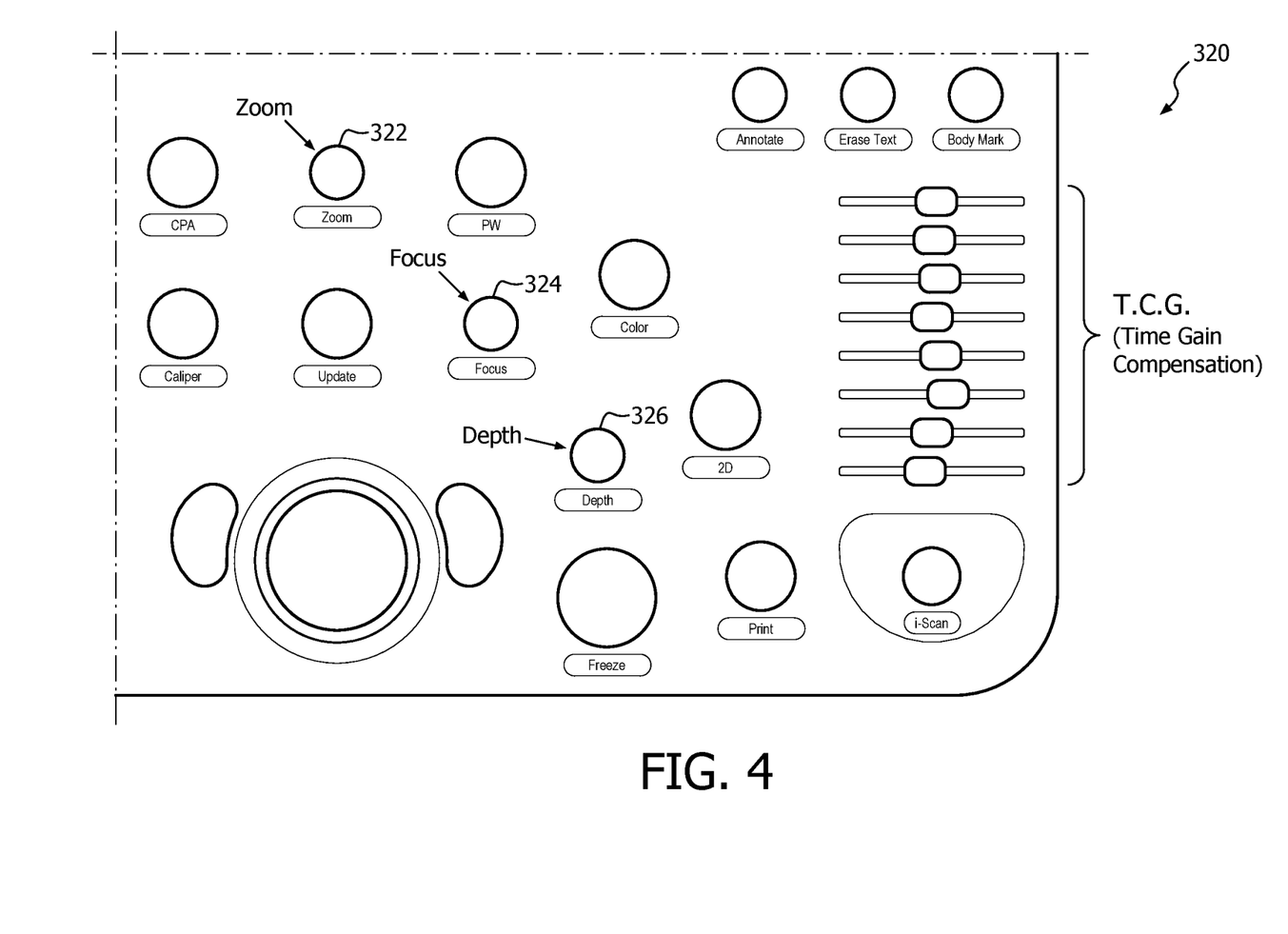
FIG. 4 shows a portion of a control panel of one embodiment of an acoustic imaging apparatus.

FIG. 4 shows a portion of a control panel of one embodiment of acoustic imaging system 320. As illustrated in FIG. 4, acoustic imaging system 320 includes a variety of manual controls for its operation. In particular, acoustic imaging system 320 includes a plurality of controls for manually adjusting one or more image resolution parameters employed by acoustic imaging system 320. In some embodiments, these manual controls may allow a user to manually adjust the focal zone of the acoustic beam employed by acoustic imaging system 320, and the corresponding acoustic images displayed on display device 340. In the embodiment shown in FIG. 4, these manual controls include a zoom control 322, a focus control 324, and a depth control 326 for adjusting the focal zone of acoustic imaging system 320.

As shown in FIG. 3, acoustic imaging system 320 also includes a communication interface 321 for connection to communication channel 305 by which it acoustic imaging system 320 may receive one or more commands for controlling its operation. Communication interface 321 may receive one or more commands which cause it to adjust one or more image resolution parameters (e.g., the focal length of the acoustic beam, the image depth of the acoustic beam, the time gain compensation, the zoom window, etc.) which are employed by acoustic imaging system 320. In some embodiments, one or more commands may be provided to acoustic imaging system 320 over communication channel 305 via communication interface 321 to cause acoustic imaging system 320 to adjust the zoom, focus, and/or depth of the acoustic image produced by acoustic imaging system 320. In some embodiments, the one or more commands may cause acoustic imaging system to adjust the focal length and/or the image depth of the acoustic beam employed by acoustic imaging system 320. Further details of this operation will be described below.

Now it should be understood that acoustic imaging system 320 employs its own particular coordinate system for generating and displaying acoustic images. That is, acoustic imaging system 320 operates in three dimensions, with the three dimensions being defined by three orthogonal directions. This set of orthogonal directions is referred to here as a coordinate frame. In general, coordinates or locations within any three dimensional space may be defined with respect to an infinite number of different coordinate frames. Acoustic imaging system 320 employs its own selected coordinate frame for defining locations within area of interest 10, and here we refer to this coordinate frame as the acoustic image coordinate frame.

EM tracking system 310 is configured to track the location of needle 20, and more particularly the location of EM sensor 22 at tip 21 of needle 20, in region of interest 10. Beneficially, EM tracking system tracks the location of needle 20, or more specifically tip 21 of needle 20, in real-time, as needle 20 is moved in region of interest 10. EM tracking system 310 may include a display device which can show the tracked location of EM sensor 22/needle tip 21 in real-time.

EM tracking system 310 employs its own selected coordinate frame for defining the location of the tip of needle 20 within area of interest 10, and here we refer to this coordinate frame as the tracking coordinate frame, or more specifically the electromagnetic tracking coordinate frame.

An operation of arrangement 300 will now be described in greater detail with reference to FIGS. 5-8. In particular, described below are an arrangement and method for generating acoustic images which automatically track the location of an object (e.g., needle 20, and specifically the tip of needle 20) within region of interest 10.

Figure 5:
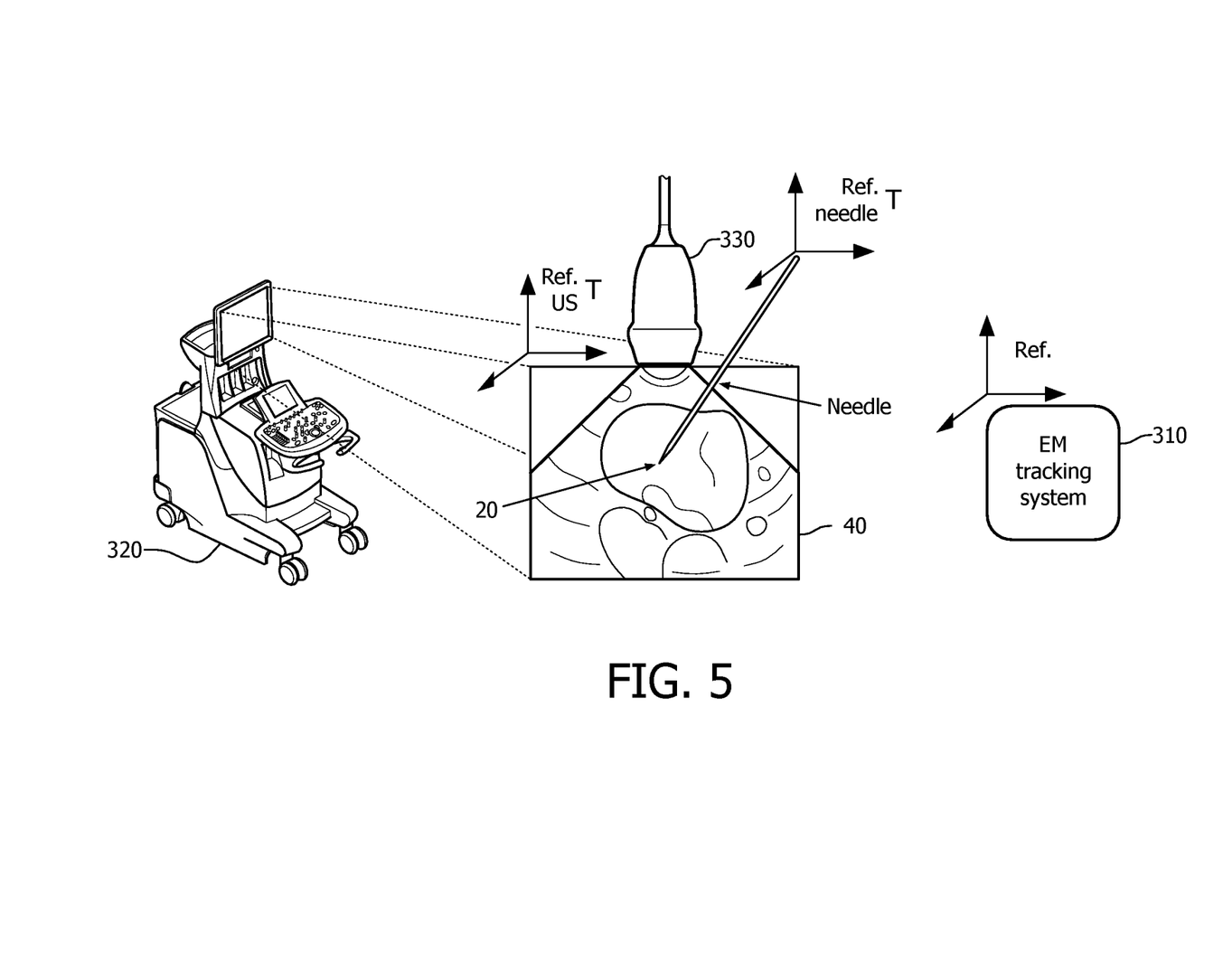
FIG. 5 illustrates operating principles of one embodiment of an arrangement for generating acoustic images which includes means for tracking the location of an object within a region of interest.

FIG. 5 illustrates operating principles of one embodiment of an arrangement for generating acoustic images which includes means for tracking the location of an object within a region of interest. As discussed above, and illustrated in more detail in FIG. 5, EM tracking system 310 is configured to track the location of needle 20 in real-time within region of interest using an electromagnetic tracking coordinate frame. Meanwhile acoustic imaging system 320 operates with an acoustic imaging coordinate frame which is different than the electromagnetic tracking coordinate frame, since in general EM tracking system 310 may operate independently from acoustic imaging system 320. However, locations in each these two coordinate frames may be transformed to locations in a common reference coordinate frame through corresponding coordinate frame transformations. The appropriate coordinate frame transformations may be produced from calibration parameters determined via a calibration procedure, for example whereby a calibration object is placed at one or a plurality (preferably, at least three) different locations, and for each location acoustic imaging system 320 is manually adjusted to be focused at the location of the object. The location data of EM tracking system 310 may then be compared with the corresponding location data for the focal zone of acoustic imaging system 320 and coordinate frame transformations may be produced for the two different coordinate frames. Although this process has been explained with respect to converting locations in both the EM tracking coordinate frame and the acoustic imaging coordinate frame to a common reference frame, it should be understood that a transformation may instead be developed with directly converts locations in the EM tracking coordinate frame to the acoustic imaging coordinate frame.

Figure 6:
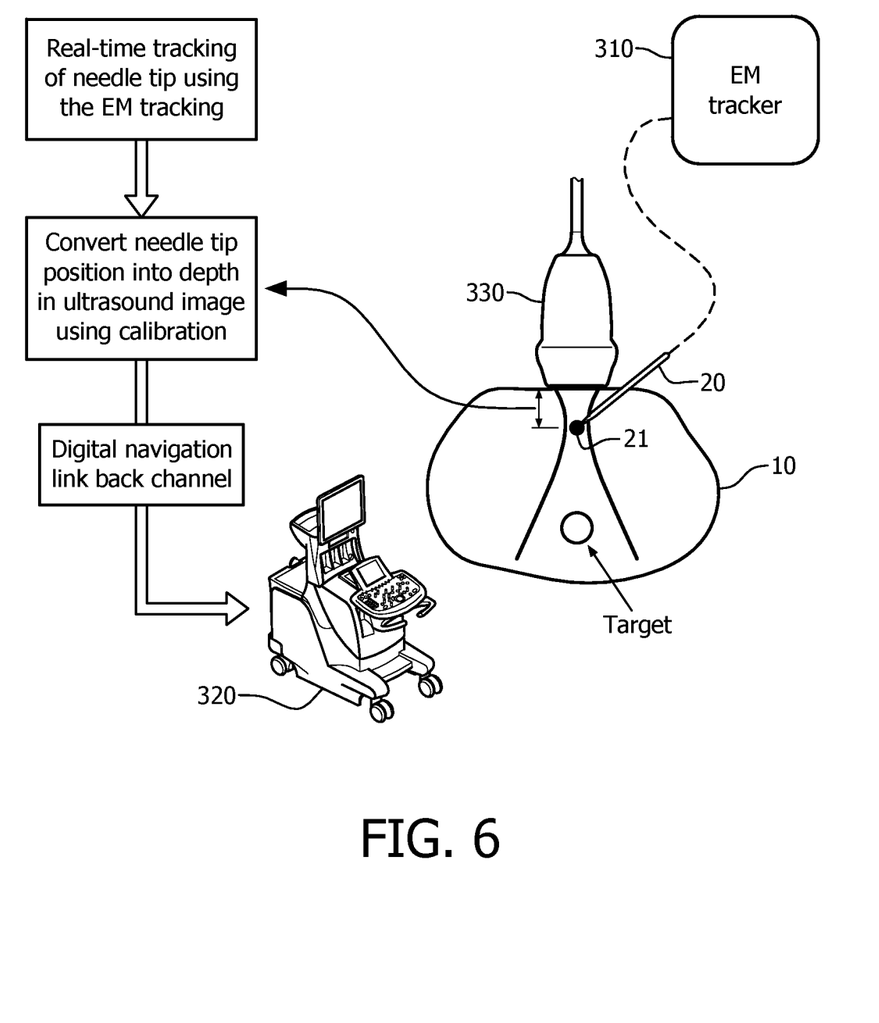
FIG. 6 illustrates operations of one embodiment of a process of generating acoustic images which track the location of an object within a region of interest.

FIG. 6 illustrates operations of one embodiment of a process of generating acoustic images which track the location of an object within a region of interest. In particular, FIG. 6 illustrates three aspects or components of a process of generating acoustic images which track the location of tip 21 of needle 20 within a region of interest. A first component involves real-time tracking of tip 21 of needle 20 using a tracking system, for example EM tracking system 310. A second component involves converting location data for tip 21 of needle 20 obtained by EM tracking system 310 from the EM tracking coordinate frame to the acoustic imaging coordinate frame employed by acoustic imaging system 320, so as to obtain a desired depth of focus for the acoustic beam produced by acoustic probe 330 under control of acoustic imaging system 320. A third component involves generating one or more commands for acoustic imaging system 320 in a format understandable by acoustic imaging system 320 to cause acoustic imaging system 320 to adjust one or more image resolution parameters (e.g. focal length, image depth, time gain compensation, zoom window, etc.) of acoustic imaging system 320 to match the real-time location of tip 21 of the medical instrument (e.g., needle 20).

Applying these components to arrangement 300 shown in FIG. 3, in one embodiment the process may operate as follows.

EM tracking system 310 tracks a location of tip 21 of needle 20 within region of interest 10 within biological tissue (e.g., a human body) in real-time. As a result, EM tracking system 310 obtains location data indicating the current location of tip 21 of needle 20 with respect to an electromagnetic tracking coordinate frame employed by electromagnetic tracking system 310.

In one embodiment, EM tracking system 310 communicates the location data to controller 350 over communication channel 315 where it is received by an input of controller 350 and provided to a processor of controller 350. The processor transforms the location data from the electromagnetic tracking coordinate frame to an acoustic image coordinate frame employed by acoustic imaging system 320, where the acoustic image coordinate frame is different from the electromagnetic tracking coordinate frame. The processor uses the transformed data to generate one or more commands for acoustic imaging system 320 to cause acoustic imaging system 320 to adjust one or more image resolution parameters (e.g. the focal length and/or the image depth of the acoustic beam, the time gain compensation, the zoom window, etc.) employed by acoustic imaging system 320 to match the location of tip 21 of needle 20. The processor then communicates the command(s) over communication channel 305 to acoustic imaging system 320. In response to the command(s), acoustic imaging system 320 adjusts the one or more image resolution parameters (e.g., adjusts the focal length and/or the image depth of the acoustic beam) such that the focal zone is located at tip 21 of needle 20.

Figure 7:
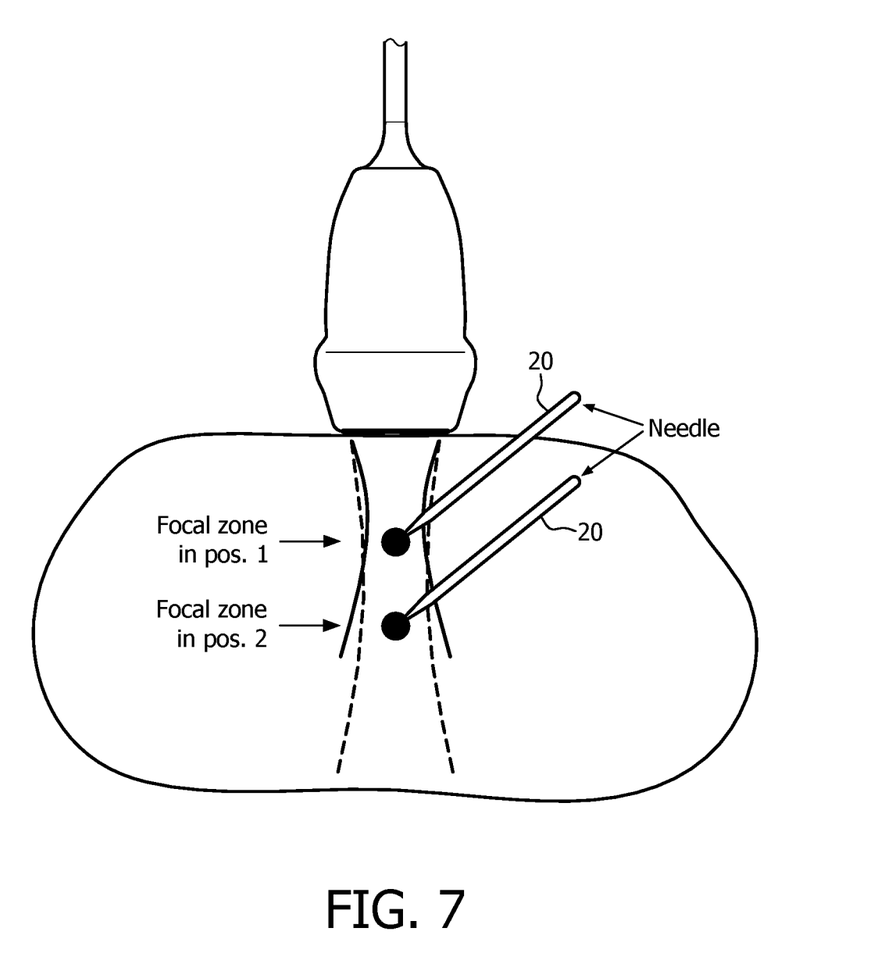
FIG. 7 illustrates an acoustic beam tracking the location of the tip of a needle during a medical procedure.

FIG. 7 illustrates an acoustic beam tracking the location of tip 21 of needle 20 during a medical procedure. When tip 21 of needle 20 is at a first position, acoustic imaging system 320 adjusts the acoustic beam to have its focal zone at the first position. As tip 21 of needle 20 is moved to a second position, through the process described above, acoustic imaging system 320 automatically adjusts the acoustic beam to have its focal zone at the second position.

Figure 8:
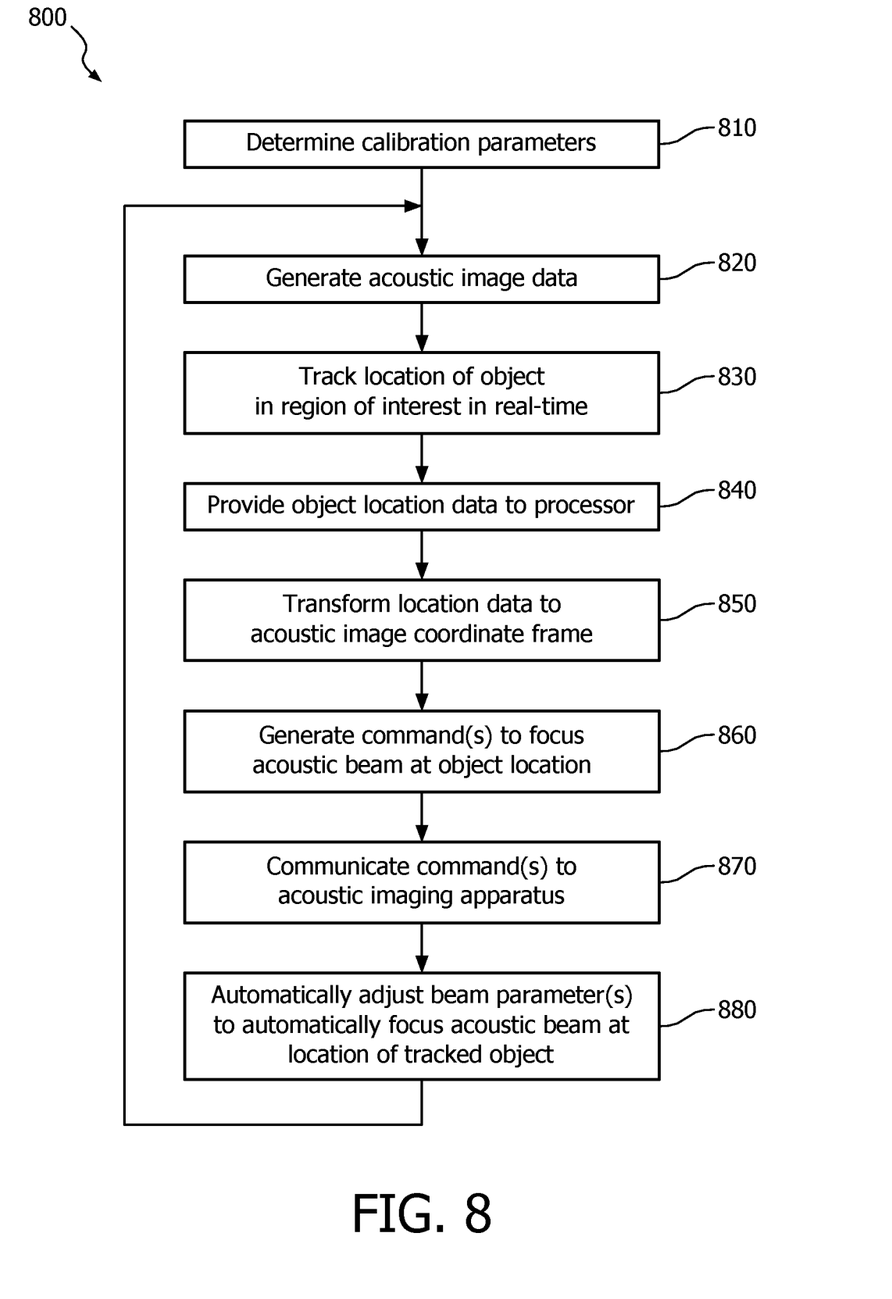
FIG. 8 is a flowchart of one embodiment of a method for generating acoustic images which track the location of an object within a region of interest.

FIG. 8 is a flowchart of one embodiment of a method 800 for generating acoustic images which track the location of an object within a region of interest. Although in general method 800 may be executed using a variety of different equipment configurations, to provide a concrete illustration method 800 will be described with respect to arrangement 300 as illustrated in FIG. 3.

In a first operation 810, calibration parameters are determined for converting location data from a tracking coordinate frame employed by a tracking system (e.g., EM tracking system 310) to the acoustic imaging coordinate frame employed by acoustic imaging system 320. In some embodiments, locations in each these two coordinate frames may be transformed to locations in a common reference coordinate frame through corresponding coordinate frame transformations. In that case, the appropriate coordinate frame transformations may be produced from calibration parameters determined in operation 810 via a calibration procedure. In one embodiment, a calibration object is placed at one or a plurality (preferably, at least three) different locations, and for each location acoustic imaging system 320 is manually adjusted to be focused at the location of the object. The location data of the tracking system may then be compared with the corresponding location data for the focal zone of acoustic imaging system 320 and coordinate frame transformations may be produced for the two different coordinate frames.

In an operation 820, acoustic image system 320 operates with acoustic probe 330 to generate acoustic image data. Acoustic image may operate in conjunction with display device 340 to display produce and display acoustic images from the acoustic image data.

In an operation 830, the tracking system (e.g., EM tracking system 310) tracks the location of an object of interest, for example a medical implement such as needle 20, within region of interest 10 in biological material in real-time. The tracking system may generate object location data which indicates the current location of the object with respect to the tracking coordinate frame employed by the tracking system.

In an operation 840, the tracking system provides the object location data to a processor, for example a processor included in controller 350.

In an operation 850, the object location data is transformed from the tracking coordinate frame to the acoustic image coordinate frame. In some embodiments, this transformation may comprise first transforming the location data to a reference coordinate frame, and then the location data from the reference coordinate frame to the acoustic image coordinate frame.

In an operation 860, the transformed object location data is employed to generate at least one command for acoustic imaging system 320 to cause acoustic imaging system 320 to adjust at least one image resolution parameter (e.g., the focal length and the image depth of the acoustic beam, time gain compensation, zoom window, etc.) employed by acoustic imaging system 320 to cause the focus of the acoustic images to match the location of the object. More specifically, one or more commands are generated to acoustic imaging system to adjust its acoustic beam to have its focal zone located at the location of the object.

In an operation 870, the command(s) are communicated via communication channel 305 to communication interface 321 of acoustic imaging system 320. The command(s) exist in a format that is understood by acoustic imaging system 320.

In an operation 880, the command(s) received by acoustic imaging system 320 cause acoustic imaging system 320 to adjust at least image resolution parameter, for example a parameter of its acoustic beam, to focus the acoustic images at the location of the object. In some embodiments, the command(s) cause acoustic imaging system 320 to adjust the focal length and/or image depth of the acoustic beam (and thereby the acoustic images) to match the location of the object (e.g., tip 21 of needle 20) with respect to the acoustic image coordinate frame. In particular, acoustic imaging system 320 may adjust the focal zone of the acoustic beam to be located at the location of tip 21 of needle 20.

Then, the process returns to operation 820 and the acoustic imaging system continues to adjust its focus to automatically track movement of the object within the region of interest in real-time and to repeatedly adjust the focus of the acoustic images to follow the movement of the object.

While preferred embodiments are disclosed in detail herein, many variations are possible which remain within the concept and scope of the invention. For example, particularly beneficial embodiments have been disclosed in detail which employ an electromagnetic tracking system to track the location of an object of interest, for example the tip of a needle. However, in general, other tracking technologies may be employed, for example an optical tracking technology, an ultrasound tracking technology wherein an object is provided with an ultrasound sensor, etc. Such variations would become clear to one of ordinary skill in the art after inspection of the specification, drawings and claims herein. The invention therefore is not to be restricted except within the scope of the appended claims.

What is claimed is:

1. A method, comprising:
   receiving location data from an electromagnetic tracking (EM) apparatus, the location data indicating a location of an EM sensor disposed with a surgical implement being tracked by the electromagnetic tracking apparatus within a region of interest within biological tissue, the location data indicating the location of the EM sensor within the region of interest with respect to an electromagnetic tracking coordinate frame employed by the electromagnetic tracking apparatus;
   transforming the location data from the electromagnetic tracking coordinate frame to an acoustic image coordinate frame employed by an acoustic imaging apparatus which is configured to employ an acoustic beam to generate acoustic image data for displaying acoustic images of the region of interest, where the acoustic image coordinate frame is different from the electromagnetic tracking coordinate frame;
   generating at least one command for the acoustic imaging apparatus based, in part, on the transformed location information, wherein the at least one command is configured to cause the acoustic imaging apparatus to focus the acoustic beam such that a focal zone of the acoustic beam is at the location of the EM sensor; and
   communicating the at least one command over a communication channel to the acoustic imaging apparatus.

2. The method of claim 1, wherein the location data indicates a location of a tip of the surgical implement.

3. The method of claim 2, wherein the surgical implement is a needle having the EM sensor disposed at the tip.

4. The method of claim 1, wherein the at least one command is configured to cause the acoustic imaging apparatus to adjust at least one of a focal length of the acoustic beam, an image depth of the acoustic beam, and a time gain compensation employed by the acoustic imaging apparatus.

5. The method of claim 3, wherein the at least one command is configured to cause the acoustic imaging apparatus to adjust at least one of a focal length and an image depth of the acoustic beam.

6. The method of claim 1, wherein the communication channel comprises an Internet connection.

7. The method of claim 1, wherein transforming the location data from the electromagnetic tracking coordinate frame to the acoustic image coordinate frame comprises using a first transform which transforms the location data from the electromagnetic tracking coordinate frame to a reference coordinate frame and a second transform which transforms the location data from the reference coordinate frame to the acoustic image coordinate frame.

8. The method of claim 1, further comprising performing a calibration procedure to produce calibration parameters, and employing the calibration parameters to transform the location data from the electromagnetic tracking coordinate frame to the acoustic image coordinate frame.

9. An apparatus, comprising:
   an input configured to receive location data from an electromagnetic tracking apparatus, the location data indicating a location of an electromagnetic (EM) sensor disposed with a surgical implement being tracked by the electromagnetic tracking apparatus within a region of interest within biological tissue, the data indicating the location of the EM sensor within the region of interest with respect to an electromagnetic tracking coordinate frame employed by the electromagnetic tracking apparatus;
   a processor configured to transform the location data from the electromagnetic tracking coordinate frame to an acoustic image coordinate frame employed by an acoustic imaging apparatus which is configured to employ an acoustic beam to generate acoustic image data for displaying acoustic images of the region of interest, where the acoustic image coordinate frame is different from the electromagnetic tracking coordinate frame, and to use the transformed data to generate at least one command for the acoustic imaging apparatus to cause the acoustic imaging apparatus to adjust at least one image resolution parameter employed by the acoustic imaging apparatus to steer a direction and a focal depth of the acoustic beam to cause the acoustic beam to be focused such that a focal zone of the acoustic beam is at the location of the EM sensor; and an output configured to communicate the at least one command over a communication channel to the acoustic imaging apparatus.

10. The apparatus of claim 9, wherein the input and the output comprise an Internet connection.

11. The apparatus of claim 9, wherein the location data indicates a location of a tip of the surgical implement.

12. The apparatus of claim 11, wherein the surgical implement is a needle having the electromagnetic sensor disposed at the tip.

13. The apparatus of claim 9, wherein the at least one image resolution parameter includes at least one of a focal length of the acoustic beam, an image depth of the acoustic beam, and a time gain compensation, employed by the acoustic imaging apparatus.

14. The apparatus of claim 13, wherein the at least one image resolution parameter includes at least one of the focal length and the image depth of the acoustic beam.

15. The apparatus of claim 9, wherein transforming the location data from the electromagnetic tracking coordinate frame to the acoustic image coordinate frame comprises using a first transform which transforms the location data from the electromagnetic tracking coordinate frame to a reference coordinate frame and a second transform which transforms the location data from the reference coordinate frame to the acoustic image coordinate frame.

16. A method, comprising:
tracking a location of an electromagnetic (EM) sensor disposed with a surgical implement while the EM sensor is disposed within a region of interest within biological tissue, the location of the EM sensor being determined with respect to a tracking coordinate frame;
applying an acoustic beam to the region of interest;
receive an acoustic signal from, at least in part, the region of interest, wherein the acoustic signal is based, at least in part, on the acoustic beam;
generating from the acoustic signal, acoustic images of the region of interest, the acoustic images being generated with respect to an acoustic image coordinate frame which is different from the tracking coordinate frame;
employing a processor to transform the location of the EM sensor from the tracking coordinate frame to the acoustic image coordinate frame; and
automatically adjusting at least one image resolution parameter of the acoustic images in response to the location of the EM sensor with respect to the acoustic image coordinate frame, wherein adjusting at least one image resolution parameter causes the acoustic beam to be steered in a direction and a depth to be focused such that a focal zone of the acoustic beam is at the location of the EM sensor.

17. The method of claim 16, wherein an acoustic imaging apparatus generates the acoustic images of the region of interest, and wherein automatically adjusting at least one image resolution parameter of the acoustic images in response to the location of the EM sensor comprises receiving at least one command at the acoustic imaging apparatus via a communication channel to which the acoustic imaging apparatus is connected.

18. The method of claim 17, wherein the at least one command causes the acoustic imaging apparatus to adjust at least one of a focal length, an image depth, and a time gain compensation, employed by the acoustic imaging apparatus.

19. The method of claim 17, wherein the communication channel employs an Ethernet protocol.

20. The method of claim 16, wherein transforming the location of the EM sensor from the tracking coordinate frame to the acoustic image coordinate frame comprises using a first transform which transforms the location data from the tracking coordinate frame to a reference coordinate frame and a second transform which transforms the location data from the reference coordinate frame to the acoustic image coordinate frame.

* * * * *